United States Patent [19]
Murphy

[11] Patent Number: 5,144,753
[45] Date of Patent: Sep. 8, 1992

[54] PROBE INSTRUMENT

[76] Inventor: Gordon J. Murphy, 638 Garden Ct., Glenview, Ill. 60025

[21] Appl. No.: 674,464

[22] Filed: Mar. 25, 1991

[51] Int. Cl.$^5$ .............................................. A61C 19/04
[52] U.S. Cl. .................................... 33/514; 128/776; 433/72; 33/836
[58] Field of Search ..................... 33/513, 514, 836; 128/776; 433/72, 141

[56] References Cited

U.S. PATENT DOCUMENTS

| | | | |
|---|---|---|---|
| 3,058,225 | 10/1962 | Ward | 33/513 |
| 3,559,292 | 2/1971 | Weissman | 33/514 |
| 3,943,914 | 3/1976 | Grenfell et al. | 33/514 |
| 4,677,756 | 7/1987 | Simon et al. | 33/514 |
| 4,764,114 | 8/1988 | Jeffcoat et al. | 33/514 |
| 4,791,940 | 12/1988 | Hirschfeld et al. | 33/513 |
| 4,823,809 | 4/1989 | Gott, Jr. et al. | 33/514 |
| 4,904,184 | 2/1990 | Murphy et al. | 128/776 |
| 4,995,403 | 2/1991 | Belkman | 128/776 |

FOREIGN PATENT DOCUMENTS

| | | | |
|---|---|---|---|
| 0296520 | 12/1988 | European Pat. Off. | 128/776 |
| 8905117 | 6/1989 | PCT Int'l Appl. | 33/514 |

*Primary Examiner*—Thomas B. Will

[57] ABSTRACT

A probe instrument for measuring the depth of a pocket in a variety of materials, including but not limited to human tissue, includes a handle, a probe movably mounted within a sheath that is movably mounted within the handle, a displacement sensor, and a force sensor. The probe terminates externally of the handle in a tip, and the sheath terminates externally of the handle in a front end. The tip of the probe is aligned with the front end of the sheath initially in a reference position. The front end of the sheath is rested on the edge of the pocket, and force is applied to the handle, causing the probe to emerge from the sheath and enter further into the pocket until the tip of the probe contacts the bottom of the pocket. The displacement sensor generates a first output signal indicative of the depth of the pocket, and the force sensor generates a second output signal indicative of the force of the probe against the bottom of the pocket. A comparator is used to generate a logic signal only when the second output signal is on a desired range. An indicator is provided to prompt the operator then to generate an actuation signal to cause a computer to read the first output signal indicative of the depth of the pocket. Alternatively, the depth of the pocket is read automatically when the force on the tip of the probe is on the desired range.

11 Claims, 2 Drawing Sheets

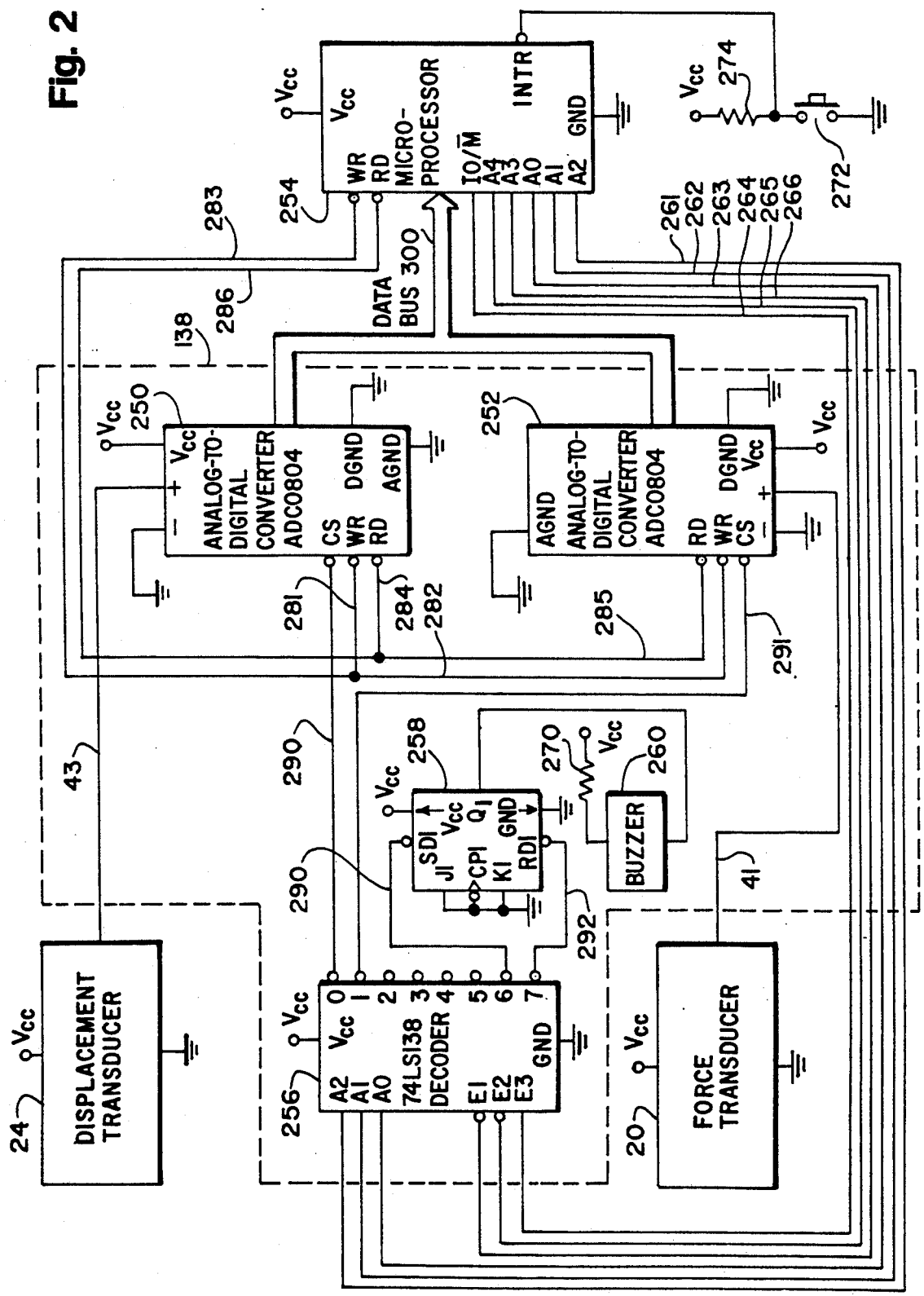

PROBE INSTRUMENT

BACKGROUND OF THE INVENTION

1. Field of the Invention

The present invention relates generally to the measurement of the depth of a recess or pocket and more particularly it relates to a probe instrument used to measure the depth of the gingival sulcus and periodontal pockets.

2. Description of the Prior Art

Chronic periodontal disease is an inflammatory disease typically induced by plaque formation. A consequence of the disease is progressive bone loss around the teeth. The resulting increase in sulcus depths in the gums creates periodontal pockets, which are indicative of the progression of the disease. To diagnose and treat periodontal disease adequately, the depths of the gingival sulcus and any periodontal pockets that exist must be determined accurately.

Pocket depths have been commonly measured by a periodontal probe that has a thin metal tip that is scored with calibration marks. The probe is inserted into the sulcus between a tooth and the gingiva and advanced until resistance is felt, which indicates that the bottom of the pocket has been reached. A depth reading is then obtained by observing visually the calibration mark that is closest to the top of the gingival margin. Six depth readings are taken around each tooth at prescribed locations, as standard practice. Each of the six readings is recorded. Frequently this recording is done by verbal reporting of the depth to an assistant, who writes it by hand on a dental chart.

Clearly, the use of such a conventional periodontal probe is a time-consuming and hence expensive procedure. Moreover, the depths of the periodontal pockets recorded during such a procedure are not always very accurate. Human error results from the need to interpolate between the calibration marks on the probe, as well as from variations in the pressure of the probe against the bottom of the periodontal pocket at the instant that the depth reading is taken. Additional error sometimes arises from the verbal communication of the measured values and the manual writing of those values on the record.

A more recently developed technique is to use a periodontal probe that contains a thin probe of circular cross-section that can be pushed out of a handle and into a sulcus by the operator of the probe. The handle is designed to provide a constant frictional force on the probe, to prevent injury to the gingival tissue.

Another recently developed periodontal probe instrument, invented by Murphy et al, contains a displacement-sensing probe element and a parallel force-sensing probe element in a common handle, together with circuitry for generating electrical signals indicative of the force and the displacement. This invention of a probe instrument is an improvement of that periodontal probe instrument.

The following patents contain descriptions of periodontal probes with a depth measurement structure:

| U.S. Pat. No. | Dated | Patentee |
| --- | --- | --- |
| 3,058,225 | Oct. 16, 1962 | Ward |
| 3,943,914 | Mar. 16, 1976 | Grenfell et al. |
| 4,203,223 | May 20, 1980 | Lautenschlager et al. |
| 4,250,895 | Feb. 17, 1981 | Lees |
| 4,340,069 | Jul. 20, 1982 | Yeaple |
| 4,665,621 | May 19, 1987 | Ackerman et al. |
| 4,677,756 | Jul. 7, 1987 | Simon et al. |
| 4,708,647 | Nov. 24, 1987 | Pippin et al. |
| 4,791,940 | Dec., 1988 | Hirschfeld et al. |
| 4,904,184 | Feb. 27, 1990 | Murphy et al. |

In addition, there is a description of a periodontal probe in a paper entitled "Computerized Periodontal Probe with Adjustable Pressure", written by E. Sild et al., which was published on pp. 53-62 of The International Journal of Periodontics and Restorative Dentistry for April, 1987.

SUMMARY OF THE INVENTION

This invention is related to the invention disclosed in U.S. Pat. No. 4,904,184 listed above but is mechanically simpler and hence less costly to manufacture and more reliable in use. Moreover, the different means that are utilized to achieve the desired result make it possible to reduce the size of that portion of the instrument that must be placed in the mouth of the patient, thus making the instrument easier for the patient to accept.

Instead of a combination of a stationary force sensing probe and a moving displacement-sensing probe, this invention utilizes a moving handle that contains both a force transducer and a displacement transducer. The object of the invention is a probe instrument that can be used to apply controllable pressure to the bottom of a pocket and that indicates the depth of the pocket accurately and automatically. The depth of the pocket is converted within the instrument to a signal that can be transmitted automatically to an electronic recording device, which may be a computer, in response to a signal generated within the instrument when the correct force is applied to the probe via the handle of the probe instrument or in response to the activation of a switch by the user of the instrument when the measured force is acceptable for taking a reading and the probe is seen to be properly positioned in the pocket. A digital output signal may be provided by the instrument in preference to an analog output signal to obtain an improved signal-to-noise ratio and consequently improved accuracy in the measurement of the depth of the pocket. An analog signal may be supplied instead of the digital signal, however, to allow a reduction in the size and the cost of the probe instrument, if that is desirable. In that case, conversion of the analog signal to a digital signal may be effected in an external analog-to-digital converter if a digital signal is desired.

The force is transmitted from the handle to the probe by means of the force transducer. This transducer embodies an elastic restraint, contained within the handle of the probe instrument, that is associated with the means for measuring the force transmitted to the probe by the handle. The combination of elastic restraint and force measurement may be implemented by means of a micromachined thin-film resistance strain gauge, for example. Alternative means are 1) a force-sensing resistor; 2) a fiber-optic force transducer; and 3) an oscillating type of piezoelectric force transducer. A simple and inexpensive means for achieving the desired result is a linear potentiometer with a spring restraint.

The distance to which the probe has entered the pocket is measured by the displacement transducer, which delivers a signal indicative of the displacement of the tip of the probe relative to the handle, in conjunction with the force transducer, which indicates the extent of its own compression or deviation from a reference state as a result of the force applied, if that deviation is not negligible. The displacement transducer may consist of a potentiometer, a combination of a potentiometer and an analog-to-digital converter, a wire-brush digital displacement encoder, or an optical displacement encoder, for example. It is to be noted that the force transducer and the displacement transducer may be identical in nature, except for the elastic restraint imposed on the displacement-sensing means in the force transducer.

An interface between the probe instrument and a digital computer may be used to provide means for storing the depth measurements and to make possible the use of various computer programs to process stored data on the depths of periodontal pockets in a selected group of patients as well as the depths of the pockets in a given patient.

An indicating device, such as a light-emitting diode or a buzzer, may be used to indicate, when the force exerted by the tip of the probe against the bottom of the pocket is within a predetermined range of values, that the depth of the pocket may be read.

The front section of the probe instrument can readily be coupled to and uncoupled from the handle. The front section consists only of the probe and a front sheath in which it slides freely, with negligible friction. Consequently, this front section can be sterilized in an autoclave, which is an important feature of this invention. Another important feature of this invention, which is a significant improvement over the periodontal probe instrument disclosed in U.S. Pat. No. 4,904,184, is the simplicity of the front section. As a result of this simplification, the manufacture of the instrument is greatly simplified and consequently it can be produced at a cost sufficiently low to allow disposal of the front section after use on a single patient. This disposability provides greater protection to patients against transmission of disease than even sterilization in an autoclave.

The rear section of the probe instrument consists of a rod, a rear sheath in which the rod is free to slide with negligible friction, a handle assembly in which the rear sheath is free to slide, the force transducer, the displacement transducer, and a spring coupling the rear sheath to the handle assembly. The probe instrument is designed so that the front section can readily be attached to the rear section and removed therefrom.

The rear end of the probe in the front section is held in position against the front end of the rod in the rear section during use by magnetic attraction of a small ferromagnetic disk attached to the rear end of the probe to a small magnet attached to the front end of the rod. The magnetic force is sufficient to overcome the negligible friction of the front sheath but small enough to allow the probe to be removed from the probe instrument easily.

The rear sheath is rigidly coupled to the actuating arm on the displacement transducer, and the body of the displacement transducer is rigidly coupled to the handle. Therefore, the displacement transducer measures the displacement of the rear sheath relative to the handle. The force transducer is rigidly mounted to the handle and is actuated by force applied to it by the rod.

When the front and rear sections of the probe instrument are coupled together, the magnet on the front end of the rod is in contact with the ferromagnetic disk on the rear end of the probe, and the front end of the rear sheath is in contact with the rear end of the front sheath. To use the depth probe instrument, it is necessary to position the front section so that the front end of the front sheath rests on the edge of the pocket with the probe outside the pocket. Application of a forward-directed force on the handle then causes the rear sheath to be forced backward relative to the handle by contact of the rear sheath with the front sheath as the handle slides forward over the front sheath. Thus, the spring and the displacement transducer are actuated. Because the force transducer is rigidly coupled to the handle, as the handle moves forward, the force transducer forces the rod forward in the virtually frictionless rear sheath. The rod, in turn, forces the probe forward in the virtually frictionless front sheath, causing the probe to emerge from the front sheath and extend into the pocket. The distance the probe extends from the front sheath is the distance the rear sheath has moved relative to the handle, and that distance is measured by the displacement transducer. Until the front part of the probe contacts the bottom of the pocket, no significant force is sensed by the force transducer. When the bottom of the pocket is reached, however, the pressure of the bottom of the pocket against the front end of the probe causes a resistance to further forward motion of the probe. This resisting force is transmitted by the probe to the rod, via the ferromagnetic disk and the magnet, and thus to the force transducer.

In the preferred embodiment, the output signal provided by the force transducer is compared with one or more reference values. When the output signal of the force transducer indicates that the force on the front end of the probe is appropriate for a reading of pocket depth, a buzzer or other indicator is actuated automatically. If the operator of the instrument is satisfied with the positioning of the probe in the pocket at that time, he actuates a switch that causes the value of the signal provided by the displacement transducer and the value of the signal provided by the force transducer, if the displacement of the force transducer is not negligible, to be entered into a digital computer, via a program in the computer that then operates to compute the value of the pocket depth and store it for processing at a later time.

In another embodiment, the value of the signal provided by the displacement transducer and the value of the signal provided by the force transducer, if the displacement of the force transducer is not negligible, are automatically entered into the digital computer when the output signal of the force transducer indicates that the force on the front end of the probe is appropriate for a reading of pocket depth.

Because the front end of the front sheath remains at rest on the edge of the pocket as the probe enters the pocket, the signal obtained from the displacement transducer before the front end of the probe contacts the bottom of the pocket indicates the depth to which the probe has entered the pocket. Because the spring that couples the rear sheath to the handle assembly serves only to hold the front sheath in position against the edge of the pocket and exerts no force on the force transducer, the output signal of the force transducer is zero until the front end of the probe contacts the bottom of the pocket. Because this spring contributes in no other way to the reading, ordinary problems of spring calibration and changes in spring characteristics over time are irrelevant. When the operator ceases to push forward on the handle, the spring returns to its original state, causing the rear sheath to return to its original position relative to the handle and to the rod in the rear section of the probe instrument. Because the ferromagnetic disk on the rear end of the probe is held in position against the magnet on the front end of the rod, the probe is thus caused to retract to its reference position, in which the front end of the probe is located just at the front end of the front sheath.

The two sections of the probe instrument can be uncoupled when desired, and the front section can then be sterilized in an autoclave, if desired. Alternatively, the front section can be made disposable to provide even further protection against infection of a second patienty by a first patient.

BRIEF DESCRIPTION OF THE DRAWINGS

The above and other advantages and features of the invention will be apparent to those skilled in the art from the following description taken in conjunction with the accompanying drawings, in which:

FIG. 2 is a diagram of an interface circuit between the probe assembly and a digital computer.

DESCRIPTION OF THE PREFERRED EMBODIMENT

Figure 1:
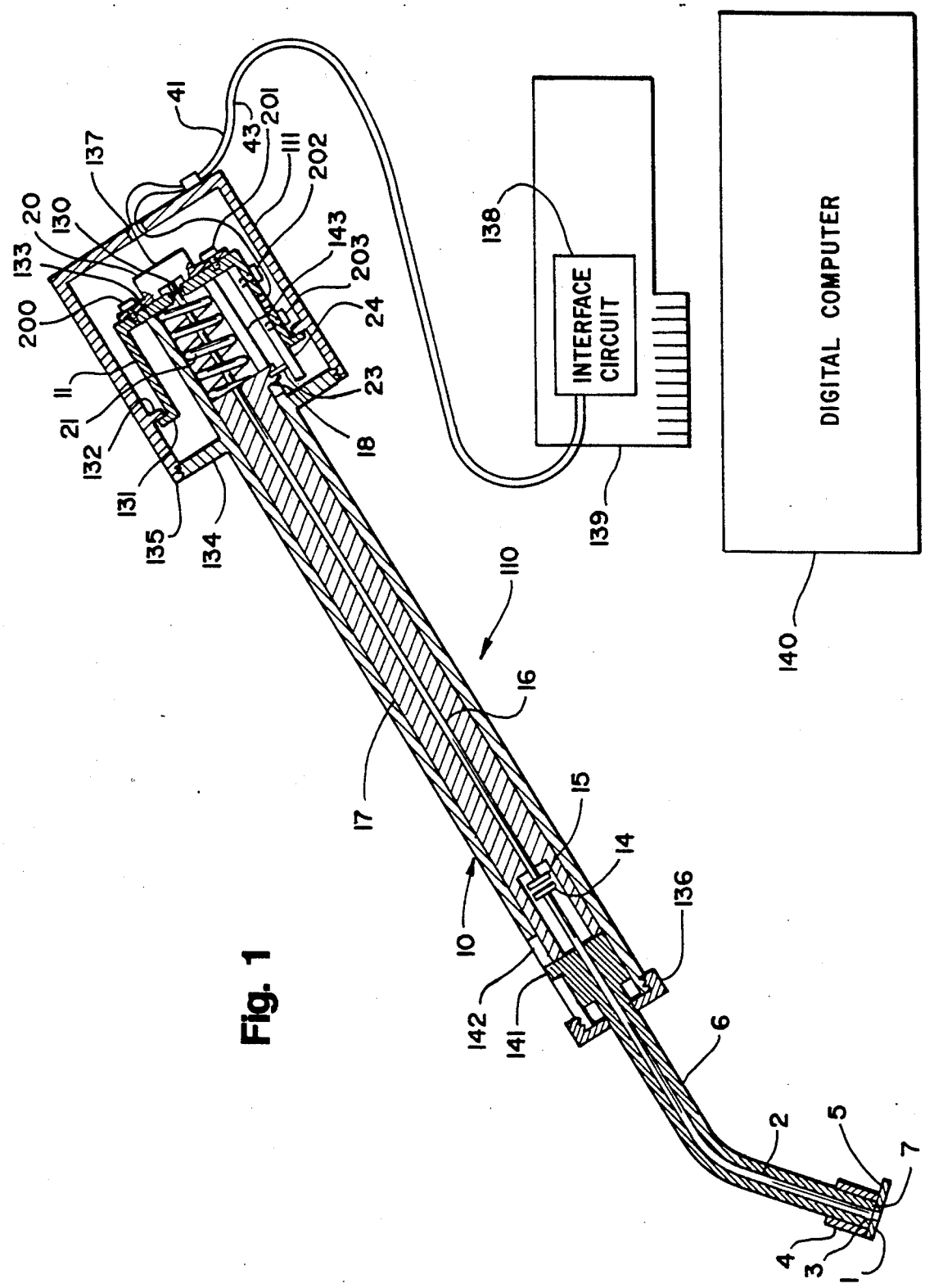
FIG. 1 is a drawing of the probe assembly.

With reference to FIG. 1, a preferred embodiment of the novel probe instrument is shown in diagrammatic form and designated generally by reference numeral 110. A front sheath 6 slides in a handle 10 that serves as the housing for the rear section of the probe instrument assembly. The front sheath is prevented from rotating within the handle by a projection 141 on the rear portion of the front sheath that is constrained by a slot 142 in the front portion of the handle 10, which extends to the front end thereof.

A flexible probe (or first probe member) 2 of round cross-section and small diameter slides within the front sheath 6. The friction between the probe and the front sheath is rendered negligible by the use of teflon or a similar material in the front sheath. The front end 3 of the probe 2 is smoothed to prevent damage or injury to the bottom of the pocket to be measured. The rear end of the probe 2 is terminated in a ferromagnetic disk 14 cemented to the probe at a right angle thereto. In a reference position, the front end of the probe 2 is aligned with the front end of the front sheath 6.

A rod (or second probe member) 16 is terminated at its front end by a permanent magnet 15 that serves to hold the probe 2 in place against the front tip of the rod by magnetic attraction of the ferromagnetic disk 14. The rear end of the rod 16 passes through a hole 130 in a cup 11, which has an integral exterior flange 131, and presses against the actuating member of a force transducer 20. The force transducer 20 is rigidly fastened to the cup 11 by two screws 200 and 201. A cap 111 has an integral interior flange 132, and the handle 10 has an integral threaded exterior flange 134. The inner surface of the front end 135 of the cap 111 is threaded to mate with the threaded flange 134 that is integral to the handle 10. The cup 11 is held in position against the rear end 133 of the handle 10 by virtue of the force applied to the flange 131 integral to the cup 11 by the flange 132 integral to the cap 111 when the cap 111 is screwed to the flange 134 integral to the handle 10. Consequently, the force transducer 20 is rigidly coupled to the handle 10, and rearward-directed axial force applied to the rod 16 is sensed by the force sensor 20 if that force is opposed by forward-directed force applied to the handle 10.

A rear sheath 17 slides over the rod 16. The friction between the rod and the rear sheath is rendered negligible in a manner similar to that used in reducing the friction between the probe and the front sheath. The rear sheath is terminated at its rear end by a projection 18, which is rigidly connected to the actuator 23 on a displacement transducer 24, which may, for example, be a potentiometer. The body of the displacement transducer 24 is rigidly fastened to the inner surface of the side wall of the cup 11 by two screws 202 and 203. Thus, the body of the displacement transducer 24 is rigidly coupled to the handle 10 when the cap 111 is screwed onto the flange 134 on the handle, holding the cup 11 in place, and the displacement transducer responds to displacement of the rear sheath 17 relative to the handle 10. Rotation of the rear sheath within the handle is prevented by virtue of the fact that the projection 18 on the rear sheath is constrained to move within a slot 143 within the handle 10, which extends to the rear end of the handle. In some embodiments, additional protection against rotation of the cup 11 when the cap 111 is screwed in place is achieved by providing one or more pins on the cap 111 that engage corresponding holes in the handle 10.

The rear end of the rear sheath 17 presses against one end of a coil spring 21, contained within the rear portion of the handle 10, the other end of which presses against the inner rear surface of the cup 11. The function of the spring 21 is to supply a light force to urge the rear sheath 17 to return to its reference position relative to the handle 10 when the forward-directed force applied to the handle 10 or the rearward-directed force applied to the front end 7 of the front sheath 6 is removed. By virtue of the force of the front end of the rear sheath 17 against the rear end of the front sheath 6, when the rear sheath 17 is in its reference position relative to the handle 10 the front sheath 6 is held against a threaded retainer 136 that screws onto the front end of the handle 10. Removal of the threaded retainer 136 allows removal of the probe 2 and the front sheath 6 from the handle 10.

The spring 21 is not an essential component of this invention. In some embodiments, the spring 21 is omitted, and the rear sheath 17 is returned to its reference position relative to the handle 10 manually or otherwise.

The wall of the rear end of the front sheath 6 is thickened to prevent the front sheath from falling out of the handle 10 through the hole in the retainer 136 through which the remainder of the front sheath 6 passes. The internal diameter of the front end of the rear sheath 17 is enlarged with respect to the internal diameter of the remainder of the rear sheath 17 to accommodate the ferromagnetic disk 14 and the magnet 15. The external diameters of the rear sheath and the rear part of the front sheath are the same, so that a forward-directed force can be applied to the rear part of the front sheath by the rear sheath, and an opposing force can be applied by the rear part of the front sheath to the rear sheath.

It is to be noted that the construction of the probe instrument can be simplified, if desired, by omission of the ferromagnetic disk 14 and the magnet 15, with the result that the internal diameter of the front end of the rear sheath 17 need not be enlarged and the external diameter of the rear end of the probe 2 and the front end of the rod 16 can be reduced to a value just enogh larger than th external diameter of the front part of the probe 2 to prevent the probe from falling out through the opening in the threaded retainer 136. Thus, the diameter of the probe instrument can be reduced to an absolute minimum. The probe 2 is then held in position with its rear end against the front end of the rod 16 by the small and otherwise negligible friction of the front sheath 6 against the probe 2. Also, if necessary, the probe 2 can be pushed back to its normal position manually or otherwise.

In normal use, one edge of the front end 7 of the front sheath 6 is placed against the edge of a pocket. If desired, a rest can be provided to widen the edge of the front end of the front sheath. Such a rest may, for example, consist of a tube 4 of short length that has a rest 5 in the form of a sector of a circular disk extending at a right angle from it at one end, the tube being of such internal diameter that it can be pressed over the front part of the front sheath 6 and held in place there by friction and being prevented from sliding too far along the front sheath by an inner lip 1 that presses against the front end 7 of the front sheath 6. Such a tube can be rotated manually so that the rest 5 is positioned at any desired location along the periphery of the front end of the front sheath. The handle 10 is then pushed in such a direction as to force the front end 7 of the front sheath 6, or the rest 5 if used, against the edge of the pocket and also forward to cause the handle 10 to slide forward on the front sheath 6. The effect of such motion is to cause the front sheath to push the rear sheath backward within the handle, compressing the spring 21; when the force applied to the handle by the user of the probe instrument is removed, the spring 21 returns to its normal state, forcing the front sheath to its normal rest position against the inner surface of the retainer 136.

As the handle is pushed forward, the rod 16 is pushed forward also, by the force transducer 20. The rod, in turn, pushes the probe 2 forward, via the magnet 15 and the ferromagnetic disk 14, causing the probe to emerge from the stationary front sheath and enter the pocket. No output signal is generated by the force transducer, however, until the front end of the probe contacts the bottom of the pocket, because the friction between the rod and the rear sheath and the friction between the probe and the front sheath are negligible.

When the front end of the probe encounters the bottom of the pocket, the force of the pocket against the front end of the probe is coupled to the force transducer 20 through the probe 2, the ferromagnetic disk 14, the magnet 15, and the rod 16. This force against the front surface of the force transducer is opposed by force that is applied to the handle 10 by the user of the probe instrument and transmitted from the handle to the force transducer through the cap 111 and the cup 11, on which the force transducer is rigidly mounted.

The force transducer 20 is electrically connected to a voltage supply, located in an interface circuit 138 on a printed-circuit board 139 that connects to a microprocessor-based digital computer 140, with a pair of conducting wires, in the customary manner. One of this pair of wires serves as an electrical ground for the various electrical circuits in the probe instrument. The electrical output signal from the force transducer is available, with respect to ground, on a third conducting wire that connects to the interface circuit 138 on the printed-circuit board 139. The displacement transducer 24 is similarly electrically connected to the voltage supply on the printed-circuit board 139, and the electrical output of the displacement transducer, with respect to ground, is available on another conducting wire that connects to the same interface circuit. Although the interface circuit is shown external to the handle assembly, in some embodiments the interface circuit 138 may be contaied within the handle assembly (inside the cap 111, for example).

The conducting wires 43 and 41 that connect the output terminals of the force transducer 20 and the displacement transducer 24, respectively, to the interface circuit 138 on the printed-circuit board 139 pass through a hole 137 centered in the rear surface of the cap 111. The function of the interface circuit 138 is to convert the output signals from the force transducer 20 and the displacement transducer 24 to digital form and transfer them to the microprocessor-based digital computer 140. The conversion is performed by two analog-to-digital converters, which are well known to those skilled in the art; and the resulting digital signals are transferred to the microprocessor in the digital computer by means of two parallel input ports that are contained also within the interface circuit 138, in a manner that is also well known.

A program stored in the digital computer 140 is in continuous operation, repeatedly reading the digital signals provided by the force transducer 20 and the displacement transducer 24, via the analog-to-digital converters. These digital signals are stored in reserved locations in the memory of the digital computer. After each reading of the output signal derived from the force transducer, the digital computer compares the value of that signal with two reference values stored within the memory of the computer. If the value obtained from the force transducer is less than the smaller of the two reference values, the force exerted on the bottom of the pocket by the probe is too small. If the value obtained from the force transducer is larger than the larger of the two reference values, the force exerted on the bottom of the pocket by the probe is too large. If, however, the value obtained from the force transducer is larger than the smaller of the two reference values and yet smaller than the larger of the two reference values, then the force exerted on the bottom of the pocket by the probe is within the acceptable range. In that event, the computer actuates an indicator in the interface circuit 138 on the printed-circuit board 139, through an output port in the iterface circuit, to inform the operator of the probe instrument that a reading of the depth of the pocket may be taken. The operator then actuates a foot-operated switch that is connected through another input port in the interface circuit 138 on the printed-circuit board 139 to the digital computer 140. In response to this actuation of the foot-operated switch, the microprocessor stores the current value of the digital signal obtained from the displacement transducer in a new location, corresponding to the particular location being probed at the time, in the memory of the digital computer and also displays on the video display unit of the digital computer 140 the location being probed and the depth that has just been measured. To coordinate the location displayed on the video display unit of the computer 140 and the location that is actually probed, a pointer within the digital computer is initialized prior to the measurement of the depth of the first in a sequence of pockets. The operator of the probe instrument is informed of the exact sequence in which the pockets are to be probed, and the pointer within the digital computer is incremented after each reading has been stored in the memory of the digital computer. Alternatively, the determination of whether the force exerted on the bottom of the pocket by the probe is within the acceptable range can be made by electronic means within the interface circuit 138 on the printed-circuit board 139. In that event, the output signal of said comparison means is transmitted to indicating means in the interface circuit or in the digital computer or to actuating means in the digital computer for reading the value of the depth of the pocket. When a hard copy of the stored data concerning the depths of the various pockets that have been probed is desired, such hard copy can be obtained by means of a printer that is a part of the digital computer 140. The entire operation of the digital computer described herein, including the printing of hard copy of the stored data, will at times hereafter, for simplicity, be referred to as processing of the first output signal and the second output signal of the probe instrument.

In the foregoing discussion, it has been assumed that the nature of the force transducer is such that no significant displacement of the rod 16 relative to the handle 10 is required to transmit the desired force to the front tip of the probe 2. If that assumption is not valid, then the computer must correct the digitized output of the displacement transducer before storing it in the memory location within the digital computer corresponding to the pocket being probed. For this purpose, a table of digital values corresponding to displacement of the rod 16 relative to the handle 10 is stored in the memory of the digital computer, as a function of the digital value corresponding to the force sensed by the force transducer 20. At the time a value of pocket depth is to be stored and displayed, the digital value obtained from the force transducer 20 is then subtracted from the digital value obtained from the displacement transducer 24, and the difference thus obtained is stored as the corrected value of the depth of the pocket and displayed as such.

From time to time, the probe instrument can be recalibrated by applying a sequence of known forces to the front end of the probe 2 and storing in the table contained in the memory of the digital computer the digital value obtained from the force transducer 20 for each.

In the preferred embodiment, an acoustical tone generator or buzzer is employed as the indicator in the interface circuit 138 on the printed-circuit board 139 that is used to inform the operator of the probe instrument that a reading of pocket depth may be taken. In an alternative design, an indication is given on the output display unit of the digital computer 140. Other kinds of indicator, such as a light-emitting diode, may also be used.

A more detailed description of the interface circuit 138 is given with reference to FIG. 2, in which the interface circuit 138 is shown enclosed in a broken line. The operation of the components illustrated in FIG. 2 is described in detail in various textbooks and reference books; in particular, MICROPROCESSORS AND PROGRAMMED LOGIC, by Kenneth L. Short, published by Prentice-Hall, Inc. in 1987 and MICROPROCESSOR-BASED PROCESS CONTROL, by Curtis D. Johnson, published by Prentice-Hall, Inc. in 1984 provide background information on microprocessors, input ports, output ports, decoders, flip-flops, and analog-to-digital converters. Background information on displacement transducers and force transducers is available in MEASUREMENT SYSTEMS, by Ernest O. Doebelin, published by McGraw-Hill Publishing Company in 1990, for example.

The output signal provided by the displacement transducer 24 is connected by a conducting wire 43 to the positive analog input terminal on a first National Semiconductor ADC0804 analog-to-digital converter 250, and the negative analog input terminal on that first analog-to-digital converter 250 is connected to the common ground, to which the analog ground terminal and the digital ground terminal on that first analog-to-digital converter 250 are also connected. Similarly, the output signal provided by the force transducer 20 is connected by a conducting wire 41 to the positive analog input terminal on a second National Semiconductor ADC0804 analog-to-digital converter 252, and the negative analog input terminal on that second analog-to-digital converter 252 is connected to the common ground, to which the analog ground terminal and the digital ground terminal on that second analog-to-digital converter 252 are also connected. Each of the analog-to-digital converters has a clock circuit, which is omitted in FIG. 2 for simplicity, the details of which are fully explained in the manufacturer's data sheet for the ADC0804 analog-to-digital converter.

An eight-bit microprocessor 254 in the digital computer 140 supplies address information to locate the two analog-to-digital converters in the memory space on six address lines 261 through 266. The address that appears on those six address lines is decoded by a Signetics 74LS138 one-of-eight decoder 256. One of the active low outputs of the decoder 256 is connected by a conductor 290 to the active low chip-select input on the first analog-to-digital converter 250, and a second active low output of the decoder 256 is connected by a conductor 291 to the active low chip select input on the second analog-to-digital converter 252. The active low WRITE terminal on the first analog-to-digital converter 250 is connected by conductors 281 and 283 to the active low WRITE terminal on the microprocessor 254, and the active low WRITE terminal on the second analog-to-digital converter 252 is similarly connected by conductors 282 and 283 to the active low WRITE terminal on the microprocessor 254. The active low READ terminal on the first analog-to-digital converter 250 is connected by conductors 284 and 286 to the active low READ terminal on the microprocessor 254, and the active low READ terminal on the second analog-to-digital converter 252 is similarly connected by conductors 285 and 286 to the active low READ terminal on the microprocessor 254. The digital output terminals of the analog-to-digital converters 250 and 252 are connected by the data bus 300 to corresponding terminals on the microprocessor 254.

A third active low output terminal of the decoder 256 is connected to the active low Direct Set terminal on a flip-flop 258, which is one of the two flip-flops in a Signetics 74LS76 dual J-K flip-flop, by a conductor 290, and a fourth active low output terminal of the decoder 256 is connected to the active low Direct Set terminal on the same flip-flop 258 by another conductor 292. The J, K, and clock input terminals on the same flip-flop 258 are connected to ground, with the result that the flip-flop 258 functions as a Set-Reset flip-flop. The microprocessor 254 and all of the integrated circuits in the interface circuit 138 are connected to the VCC and Ground terminals of a power supply, which was omitted from FIG. 2 for simplicity, in the customary manner. The displacement transducer 24 and the force transducer 20 are similarly connected to the VCC and Ground terminals of the power supply.

The purpose of the flip-flop 258 is to drive a buzzer 260, which serves to indicate when a reading of pocket depth may be taken. The program stored in the memory of the digital computer 140 cause the microprocessor 254 to initiate conversion of the output signal of the force transducer 20 on its output conductor 41 from time to time, to read the corresponding digital output of the second analog-to-digital converter 252, and to determine from that digital output of the second analog-to-digital converter 252 whether the force on the bottom of the pocket is on the proper range for a reading of pocket depth. When the digital output of the second analog-to-digital converter 252 is on the proper range, the program stored in the memory of the digital computer 140 causes the microprocessor 254 to clear or reset the flip-flop 258 via the decoder 256. As a result, the Q output of the flip-flop 258 goes low, and current flows in the resistor 270 and the buzzer 260, causing the buzzer 260 to emit an audible signal. After a short predetermined length of time, the program stored in the memory of the digital computer 140 causes the microprocessor 254 to set the flip-flop 258, via the decoder 256. The Q output of the flip-flop 258 consequently goes high, terminating the current in the buzzer 260 and thus causing the termination of the audible signal.

The human operator of the probe instrument responds to the sound of the buzzer 260 by momentarily actuating a switch 272, which connects an active low interrupt input terminal on the microprocessor 254 to ground. The interrupt input terminal on the microprocessor 254 is normally held inactive by its connection through a resistor 274 to VCC.

In response to the interrupt signal generated by the closing of the switch 272, the program stored in the memory of the digital computer 140 causes the microprocessor to initiate conversion of the output signal of the displacement transducer 24 on its output conductor 43 to digital form, to read the corresponding digital output of the first analog-to-digital converter 250, and to store that digital value in the corresponding location in the memory of the digital computer 140, as well as to display that reading in an appropriate format on the output display of the digital computer 140.

The ADC0804 analog-to-digital converter combines in a single unit analog-to-digital conversion means and a tristate input port for a microprocessor. If other means are used for analog-to-digital conversion, a separate input port may be required. The locations of the analog-to-digital converters 250 and 252 in the memory space can be changed by substituting other address pins on the microprocessor for those shown connected to the decoder 256 in FIG. 2. A conventional output port may be used to couple one line on the data bus 300 to the buzzer 260, instead of using the circuit illustrated for that purpose in FIG. 2. Other devices connected to the data bus 300, such as memory, a printer, a keyboard, and an output display unit, for example, are not shown in FIG. 2, because they are commonly found in digital computers and their operation is widely understood. Nevertheless, the memory is an essential part of the digital computer 140 shown in FIG. 1 and the output display and the printer are important parts of the digital computer 140 in at least some embodiments of this invention.

It will be apparent to one skilled in the art that an improvement can be made by the use of two discernibly different indicator devices so as to indicate when the force on the front tip of the probe 2 is too low, to signal that the probe must be pressed further into the pocket, and to indicate when the force on the front tip of the probe 2 is too large, to signal that the probe must be partially withdrawn from the pocket.

Another improvement that may be desirable in some circumstances is to modify the program stored in the digital computer so that when the digital value obtained from the force transducer 20 is on the acceptable range, the computer automatically stores the correct value of the depth of the pocket and displays it, instead of indicating to the operator of the probe instrument that a reading may be taken. When the reading of pocket depth is taken automatically in this manner, the indicator is used to inform the operator that a reading has been taken.

It is to be noted that a particularly simple and inexpensive embodiment of this invention can be realized by using identical potentiometers for the displacement transducer 24 and the force transducer 20, with the addition of a spring to convert displacement to force in the force transducer. Moreover, slide potentiometers appropriate for use as the force transducer 20 and the displacement transducer 24 are now commercially available with an internal spring designed to return the movable wiper of the potentiometer to a reference position at one end of its range of motion. If such a potentiometer is used as the displacement transducer 24, its internal spring will serve also the purpose for which the spring 21 was included. Thus, the spring 21 can be eliminated, which results in a further simplification of the probe instrument. When this approach is used, it is desirable that the spring in the potentiometer used as the force transducer 20 be much stiffer than the spring in the potentiometer used as the displacement transducer 24.

It is to be noted also that the interface circuit 138 and the digital computer 140 together constitute computing means, which may assume a variety of forms; for example, analog computing means may be used in another embodiment of this invention.

In some embodiments of this invention, a second projection, like the trigger on a gun, may be rigidly coupled to one side of the front sheath 6, and a slot at the front end of the handle 10 may be provided within which said projection may move longitudinally, with said projection extending beyond the external wall of the handle to be engaged by a human finger. The user of the probe instrument then grasps the handle 10 with index finger on said projection and pulls back on said projection, thus exerting the force required to extend the probe 2, instead of forcing the front end 7 of the front sheath 6 against the edge of the pocket to do so.

In some embodiments of this invention, where removability of the front end of the instrument is not required, the front sheath 6 and the rear sheath 17 may be combined into a single sheath and the first probe member (or probe) 2 and the second probe member (or rod) 16 may be combined into a single probe member, which further simplifies the construction of the probe instrument.

It is to be understood that various forms of electronic and electro-mechanical devices may be used in the processing of the output signals provided by the force transducer 20 and the displacement transducer 24. The digital computer 140 may include a printer, for example, for making a hard copy of the data obtained by use of the probe instrument. In general, the entire operation of converting the output signals of the force ttransducer 20 and the displacement transducer 24 to a desired form, however that is done, is referred to as processing those output signals.

Finally, in some embodiments of this invention, the output signals provided by the force transducer 20 and the displacement transducer 24 may be processed by computing means to tabulate or chart the depth of a pocket as a function of the force of the probe against the bottom of the pocket.

The probe instrument invention described herein is not disclosed in any of the patents listed above, nor in the referenced paper written by Sild et al. U.S. Pat. No. 4,904,184 contains the disclosure most closely related to this invention, which may be viewed as an improvement on the probe instrument disclosed in that patent. Some of the differences in the probe instrument of this invention with respect to the periodontal probe instrument disclosed in U.S. Pat. No. 4,904,184 are as follows:

1. The wire-type depth sensor disclosed in U.S. Pat. No. 4,904,184 has been eliminated. Elimination of that wire results in a very significant simplification in the construction of the probe assembly and hence a very significant reduction in the cost of manufacturing the probe assembly.

2. Because of the low cost, it becomes feasible to dispose of the front section of the probe assembly after it has been used on a single patient. Disposability of the front section of the probe assembly provides protection against infection of a second patient that is superior even to sterilization in an autoclave.

3. A depth sensor in the form of a sheath that completely surrounds the active part of the probe has been provided. This sheath makes it possible to use the probe on any side of the pocket without the use of the sliprings suggested in U.S. Pat. No. 4,904,184.

4. An improved method for separating the front part of the probe assembly from the rear part of the probe assembly so that the front part of the probe assembly can be fully sterilized or discarded has been provided. The improved method is faster and easier to use than the method described in U.S. Pat. No. 4,904,184 and results in a more rugged device, as well.

5. The simplification of the front part of the instrument makes it possible to make the portion of the instrument that enters the mouth of the patient smaller in size, with the result that the instrument is easier for the patient to accept.

It is apparent that although measurement of the depth of periodontal pockets is the intended primary use of the probe instrument disclosed herein, a probe instrument of this kind can be used instead for the measurement of the depth of pockets in wood, metal, plastic, earth, and other materials.

While only particular embodiments of the invention have been described and illustrated, it is apparent that modifications may be made therein. It is the object of the inventor in the appended claims to cover all such modifications and applications as may fall within the true scope and spirit of the invention.

What is claimed is:

1. A probe instrument for measuring the depth of a pocket in a variety of different kinds of material, including but not restricted to human tissue, said instrument comprising:

a handle having a front end and a rear end;

a first probe member being movably mounted within a first sheath which is movably mounted within said handle, said first probe member terminating externally of said handle in a front end of said first probe member and internally within said handle in a rear end of said first probe member and said first sheath terminating externally of said handle in a front end of said first sheath and internally within said handle in a rear end of said first sheath;

a second probe member being movably mounted within a second sheath which is movably mounted within said handle, said second probe member having a front end so positioned that it is normally in contact with said rear end of said first probe member and said second probe member being so aligned that it can transmit longitudinal force to said rear end of said first probe member and said second sheath so positioned that its front end is normally in contact with said rear end of said first sheath and that it can receive longitudinal force from said rear end of said first sheath;

elastic restraining means mounted within said handle in such a manner as to tend to move said second sheath forward relative to said handle and hold said front end of said second sheath against said rear end of said first sheath, thus tending to move said first sheath forward relative to said handle until a projection on said first sheath inside said handle contacts a stop on said handle, thereby returning said front end of said first sheath to a reference position relative to said handle.

displacement sensing means mechanically connected to said second sheath and to said handle and being responsive to displacement of said second sheath relative to said handle for generating a first output signal indicative of said displacement of said second sheath relative to said handle; and force sensing means mechanically connected to said handle and to said rear end of said second probe member and being responsive to longitudinal force applied to said front end of said first probe member and transmitted through said first probe member and said second probe member to said force sensing means for generating a second output signal indicative of the magnitude of said force, to indicate when said front end of said first probe member is pressing against the bottom of a pocket, with the result that, if said front end of said first probe member and said front end of said first sheath are initially aligned and then said front end of said first sheath is held in a fixed position against the edge of said pocket and said handle is slid along said second sheath, forcing said first probe member forward out of said first sheath until said front end of said first probe member is pressing against the bottom of said pocket by virtue of force transmitted from said handle to said first probe member via said force sensing means and said second probe member, said first output signal indicates the depth of said pocket at the probe force indicated by said second output signal.

2. The probe instrument of claim 1 further comprising data processing means, analog and/or digital in nature and possibly including a human operator, adapted to receive said first output signal and said second output signal and responsive to said first output signal and said second output signal to record the depth of said pocket as indicated by said first output signal when the force of said first probe member on the bottom of said pocket as indicated by said second output signal is on a predetermined range.

3. The probe instrument of claim 1 further comprising means mountable on said front sheath for providing a rest for said front sheath at a selectable location on the periphery of said front end of said front sheath, to increase the area of contact of said front end of said front sheath with said edge of said pocket.

4. A probe instrument as claimed in claim 1 further comprising means to facilitate the removal of said first probe member and said front sheath from the remainder of said probe instrument.

5. A probe instrument as claimed in claim 1 further comprising means for coupling said rear end of said first probe member to said front end of said second probe member.

6. A probe instrument as claimed in claim 1 wherein said displacement sensing means and said force sensing means each comprise a potentiometer with elastic restraint.

7. A probe instrument as claimed in claim 1 wherein said force sensing means comprises a strain gauge.

8. A probe instrument for measuring the depth of a pocket in a variety of different kinds of material, including but not restricted to human tissue, said probe instrument comprising:
a handle having a front end and a rear end;
a probe being movably mounted within a sheath which is movably mounted within said handle, said probe terminating externally of said handle in a front end of said probe and terminating internally of said handle in a rear end of said probe and said sheath terminating externally of said handle in a front end of said sheath and terminating internally of said handle in a rear end of said sheath;
displacement sensing means connected to said sheath and said handle and being responsive to displacement of said sheath relative to said handle for generating a first output signal indicative of said displacement of said sheath relative to said handle; and
force sensing means in contact with said rear end of said probe when said front end of said probe is aligned with said front end of said sheath, said force sensing means being mechanically connected to said handle and being responsive to longitudinal force applied to said front end of said probe and transmitted through said probe to said force sensing means for generating a second output signal indicative of the magnitude of said force, to indicate when said front end of said probe is pressing against the bottom of a pocket, with the result that, if said front end of said probe and said front end of said sheath are initially aligned and then said front end of said sheath is held in a fixed position against the edge of said pocket and said handle is slid along said sheath, forcing said front end of said probe against the bottom of said pocket by virtue of force transmitted to said probe from said handle via said force sensing means, said first output signal indicates the depth of said pocket at the force indicated by said second output signal.

9. The probe instrument of claim 8 further comprising computing means, possibly including a human operator, adapted to receive said first output signal and said second output signal and responsive to said first output signal and said second output signal for tabulating or charting the depth of said pocket as a function of said force.

10. The probe instrument of claim 8 further comprising elastic restraining means mounted within said handle in such a manner as to tend to move said sheath forward relative to said handle until a projection on said sheath inside said handle contacts a stop on said handle, thereby returning said front end of said sheath to a reference position relative to said handle.

11. The probe instrument of claim 8 wherein said rear end of said probe is rigidly attached to said force sensing means.

* * * * *